(12) United States Patent
Long et al.

(10) Patent No.: US 9,956,328 B2
(45) Date of Patent: *May 1, 2018

(54) MULTI-CONDUIT CONNECTORS AND METHODS FOR NEGATIVE PRESSURE WOUND THERAPY

(71) Applicant: KCI Licensing, Inc., San Antonio, TX (US)

(72) Inventors: Justin Alexander Long, Lago Vista, TX (US); Aidan Marcus Tout, Alderbury (GB); Larry Tab Randolph, San Antonio, TX (US); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 394 days.

This patent is subject to a terminal disclaimer.

(21) Appl. No.: 14/930,479

(22) Filed: Nov. 2, 2015

(65) Prior Publication Data

US 2016/0114089 A1    Apr. 28, 2016

Related U.S. Application Data

(63) Continuation of application No. 13/874,974, filed on May 1, 2013, now Pat. No. 9,205,246, which is a (Continued)

(51) Int. Cl.
*A61M 1/00* (2006.01)
*B23P 17/04* (2006.01)
(Continued)

(52) U.S. Cl.
CPC ............ *A61M 1/0086* (2014.02); *A61M 1/00* (2013.01); *A61M 3/0279* (2013.01);
(Continued)

(58) Field of Classification Search
CPC ...... A61M 1/00; A61M 1/0086; A61M 35/00; A61M 39/105; A61M 39/20; A61M 3/0279; Y10T 137/87571; Y10T 137/8759
See application file for complete search history.

(56) References Cited

U.S. PATENT DOCUMENTS

| 1,355,846 A | 10/1920 | Rannells |
| 2,547,758 A | 4/1951 | Kelling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.

(Continued)

*Primary Examiner* — Susan Su
*Assistant Examiner* — Kai Weng

(57) ABSTRACT

Multi-conduit connector apparatuses for use in negative pressure wound therapy (NPWT) apparatuses to wound dressing, and methods for installing multi-conduit connector apparatuses in NPWT apparatuses.

22 Claims, 4 Drawing Sheets

Related U.S. Application Data continuation of application No. 13/017,857, filed on Jan. 31, 2011, now Pat. No. 8,454,567.

(60) Provisional application No. 61/300,362, filed on Feb. 1, 2010.

(51) Int. Cl.
*A61M 39/10* (2006.01)
*A61M 3/02* (2006.01)
*A61M 35/00* (2006.01)
*A61M 39/20* (2006.01)

(52) U.S. Cl.
CPC .......... *A61M 35/00* (2013.01); *A61M 39/105* (2013.01); *A61M 39/20* (2013.01); *B23P 17/04* (2013.01); *Y10T 29/49826* (2015.01); *Y10T 137/87571* (2015.04); *Y10T 137/87579* (2015.04); *Y10T 137/87587* (2015.04); *Y10T 137/87668* (2015.04); *Y10T 137/87676* (2015.04); *Y10T 137/87684* (2015.04); *Y10T 137/87692* (2015.04)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,045,077 A * | 9/1991 | Blake, III ........... A61M 1/0001 128/205.12 |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carlon |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0106116 A1* | 4/2010 | Simmons ............ A61M 1/0001 604/319 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |

(56) References Cited

FOREIGN PATENT DOCUMENTS

| WO | 80/02182 A1 | 10/1980 |
|---|---|---|
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

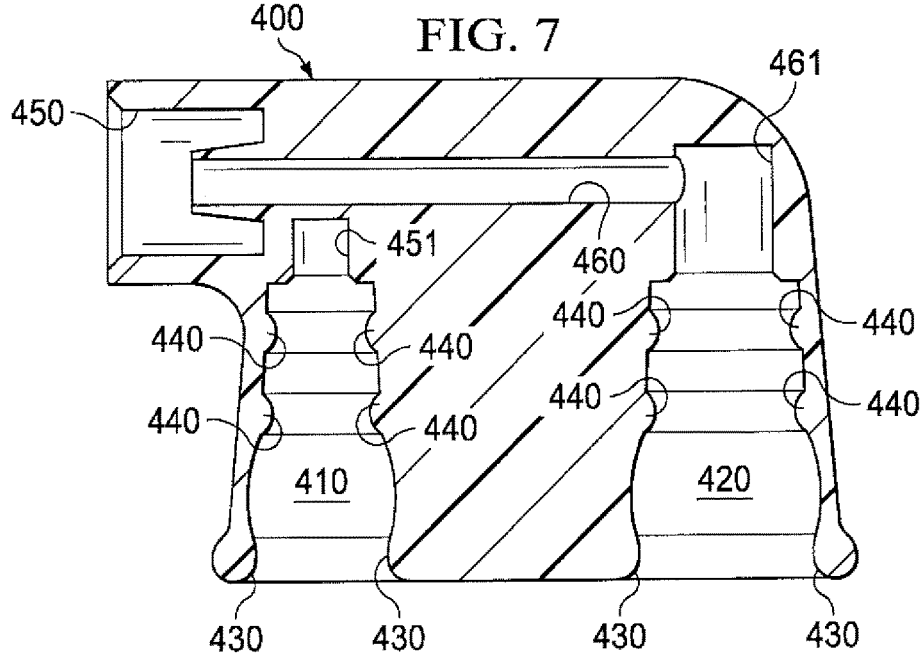
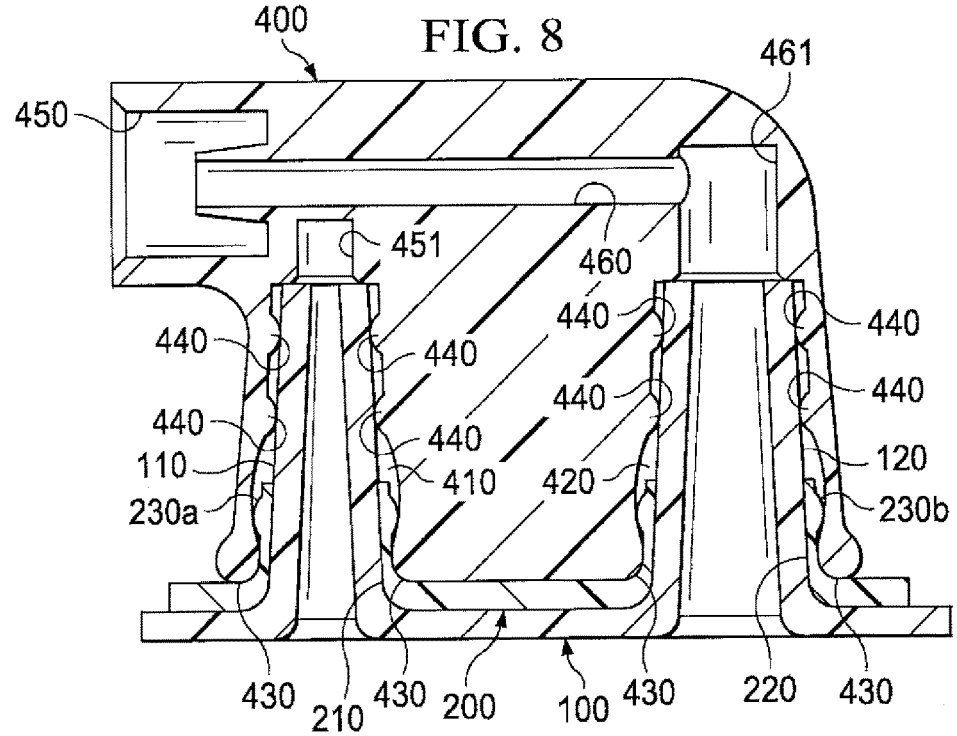

MULTI-CONDUIT CONNECTORS AND METHODS FOR NEGATIVE PRESSURE WOUND THERAPY

CROSS-REFERENCE(S) TO RELATED APPLICATION(S)

This application is a continuation of U.S. patent application Ser. No. 13/874,974, filed May 1, 2013, which is a continuation of U.S. patent application Ser. No. 13/017,857, filed Jan. 31, 2011, now U.S. Pat. No. 8,454,567, which claims priority to U.S. Provisional Patent Application Ser. No. 61/300,362 filed Feb. 1, 2010. This provisional application is expressly incorporated by reference.

BACKGROUND

1. Field of the Invention

The present invention relates generally to healing of wounds and wound-treatment therapies. More particularly, but not by way of limitation, the present invention relates to apparatuses and methods for a multi-conduit connector used in negative pressure wound therapy (NPWT) apparatuses and methods.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device).

While NPWT has been highly successful in the promotion of wound closure, healing many wounds previously thought largely untreatable, some difficulty remains. One common component of an NPWT system is a device or structure (e.g., a multi-conduit connector) that connects a canister housing a vacuum, a fluid receptacle, or both to a medical tubeset. The tubeset may be used to deliver negative pressure to the wound site, to remove exudates from the wound site, or both.

While NPWT has been used for some time, multi-conduit connectors can be expensive to manufacture and difficult to install. Often, a user is unable to determine whether a connection has been made between the multi-conduit connector and the canister.

SUMMARY

The present disclosure includes embodiments of multi-conduit connectors. Specific embodiments comprise multi-conduit connector apparatuses for use in negative pressure wound therapy (NPWT) apparatuses and methods for installing multi-conduit connector apparatuses in NPWT apparatuses.

Specific embodiments include a multi-conduit connector apparatus comprising a canister lid comprising a first nipple and a second nipple; a cap sleeve, comprising a first annular sleeve and a second annular sleeve, where the first annular sleeve engages the first nipple and the second annular sleeve engages the second nipple; and a housing, comprising a first port, comprising a plurality of sealing ridges, the plurality of sealing ridges creating a seal with the first nipple; a second port, comprising a plurality of sealing ridges, the plurality of sealing ridges creating a seal with the second nipple; a first conduit comprising a first outlet, where the first outlet is in fluid communication with the first nipple; and a second conduit comprising a second outlet, where the second outlet is in fluid communication with the second nipple.

In certain embodiments, the first conduit is coupled to the first port. The second conduit may be coupled to the second port. The first conduit, the second conduit, or both may be coupled to a wound dressing. The first conduit and/or the second conduit may be comprised of a single lumen or multiple lumens.

Other embodiments may comprise a multi-conduit connector apparatus comprising: a canister lid comprising a first nipple and a second nipple; a cap sleeve, comprising: a first annular sleeve comprising a first clearance shoulder, where the first annular sleeve engages the first nipple; and a second annular sleeve comprising a second clearance shoulder, where the second annular sleeve engages the second nipple; and a housing, comprising: a first port, comprising: a plurality of sealing ridges, the plurality of sealing ridges creating a seal with the first nipple; and a first engagement tab, the first engagement tab engaging the first clearance shoulder; a second port, comprising: a plurality of sealing ridges, the plurality of sealing ridges creating a seal with the second nipple; and a second engagement tab, the second engagement tab engaging the second clearance shoulder; a first conduit comprising a first outlet, where the first outlet is in fluid communication with the first nipple; and a second conduit comprising a second outlet, where the second outlet is in fluid communication with the second nipple.

In certain embodiments, the first outlet is coupled to the first nipple. In other embodiments, the second outlet is coupled to the second nipple. In specific embodiments, the first conduit or the second conduit may be coupled to a wound site. In some embodiments, the first nipple or the second nipple may be a tapered nipple.

In some embodiments, the cap sleeve may further comprises a sleeve lid and/or a hinge. The cap sleeve lid may be comprised of plastic or rubber in certain embodiments.

In certain embodiments, the clearance shoulder is substantially a ring. In other embodiments, the clearance shoulder is deformable.

Still other embodiments comprise a multi-conduit connector apparatus comprising: a canister lid comprising a first nipple and a second nipple, where the first nipple further comprises a first clearance shoulder, and the second nipple further comprises a second clearance shoulder; and a housing, comprising: a first port, comprising: a plurality of sealing ridges, the plurality of sealing ridges creating a seal with the first nipple; and a first engagement tab, the first engagement tab engaging the first clearance shoulder; a second port, comprising: a plurality of sealing ridges, the plurality of sealing ridges creating a seal with the second nipple; and a second engagement tab, the second engagement tab engaging the second clearance shoulder; a first conduit comprising: a first outlet, where the first outlet is coupled to the first nipple, and where the multi-lumen coupling member is configured to be coupled to a wound site; and a second conduit comprising: a second outlet, where the second outlet is coupled to the second nipple, and where the second conduit member is configured to be coupled to a wound site.

Other embodiments may comprise obtaining a multi-conduit connector apparatus comprising: a canister lid comprising a first nipple and a second nipple; a cap sleeve, comprising: a first annular sleeve comprising a first clearance shoulder, where the first annular sleeve engages the first nipple; and a second annular sleeve comprising a second clearance shoulder, where the second annular sleeve engages the second nipple; and a housing, comprising: a first port, comprising: a plurality of sealing ridges, the plurality of sealing ridges creating a seal with the first nipple; and a first engagement tab, the first engagement tab engaging the first clearance shoulder, a second port, comprising: a plurality of sealing ridges, the plurality of sealing ridges creating a seal with the second nipple; and a second engagement tab, the second engagement tab engaging the second clearance shoulder, a first conduit comprising a first outlet, where the first outlet is in fluid communication with the first nipple; and a second conduit comprising a second outlet, where the second outlet is in fluid communication with the second nipple; placing the cap sleeve on the canister lid; placing the housing on the cap sleeve and canister lid; and applying a downward force until the housing has fully engaged the canister lid. Still other embodiments comprise placing the housing on the cap sleeve and the canister lid and applying a downward force to the housing until the housing has fully engaged the canister lid.

Yet other embodiments comprise a method for sealing a multi conduit connector, comprising: obtaining a multi-conduit connector apparatus comprising: a canister lid comprising a first nipple and a second nipple, where the first nipple further comprises a first clearance shoulder, and the second nipple further comprises a second clearance shoulder; and a housing, comprising: a first port, comprising: a plurality of sealing ridges, the plurality of sealing ridges creating a seal with the first nipple; and a first engagement tab, the first engagement tab engaging the first clearance shoulder; a second port, comprising: a plurality of sealing ridges, the plurality of sealing ridges creating a seal with the second nipple; and a second engagement tab, the second engagement tab engaging the second clearance shoulder; a first conduit comprising: a first outlet, where the first outlet is coupled to the first nipple, and where the multi-lumen coupling member is configured to be coupled to a wound site; and a second conduit comprising: a second outlet, where the second outlet is coupled to the second nipple, and where the second conduit member is configured to be coupled to a wound site; placing the housing of on the canister lid; and applying a downward force until the housing has fully engaged the canister lid.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears, and structural features may be drawn larger or smaller than scale. Identical reference numbers do not necessarily indicate an identical structure. Rather, the same reference number may be used to indicate a similar feature or a feature with similar functionality, as may non-identical reference numbers.

FIG. 7 depicts a cross-sectional view of one embodiment of the multi-conduit housing.

FIG. 8 depicts a cross-sectional assembly view of the canister lid of FIG. 3, the cap sleeve of FIG. 4 and the multi-conduit housing of FIG. 6.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a connector that "comprises," "has," "includes" or "contains" one or more elements possesses those one or more elements, but is not limited to possessing only those elements. For example, in a connector that comprises a nipple and a port, the connector includes the specified elements but is not limited to having only those elements. For example, such a connector could also include an annular sleeve.

Further, a device or structure that is configured in a certain way is configured in at least that way, but it can also be configured in other ways than those specifically described.

Embodiments of the multi-conduit connector apparatus depicted may be used in a variety of applications. A non-limiting example of a use for a multi-conduit connector apparatus is in the field of negative pressure wound therapy (NPWT). The connector apparatus can link more than one conduit to a wound dressing and a wound treatment apparatus.

Figure 1:
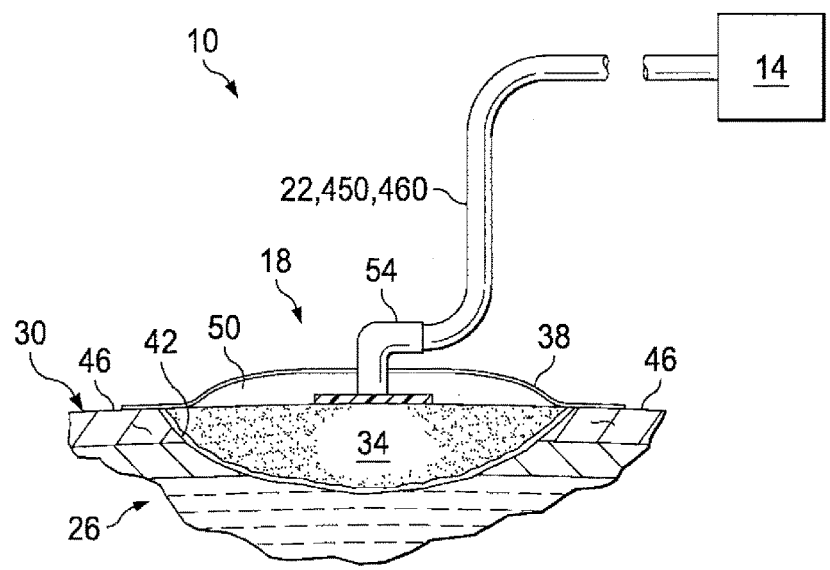
FIG. 1 depicts a schematic view of a wound treatment system.

FIG. 1 shows an embodiment of a wound treatment system 10. In the embodiment shown, apparatus 10 comprises a wound-treatment apparatus 14, and a wound dressing 18 coupled to apparatus 14 by a conduit 22. In the embodiment shown, conduit 22 further comprises a conduit 450 and a conduit 460. As shown, dressing 18 is configured to be coupled to (and is shown coupled to) a wound 26 of a patient 30. More particularly, in the embodiment shown, dressing 18 comprises a wound insert 34 and a drape 38. As shown, wound insert 34 is configured to be positioned (and is shown positioned) on wound 26 (e.g., on or adjacent to wound surface 42), and/or drape 38 is configured to be coupled to (and is shown coupled to) skin 46 of the patient adjacent to wound 26 such that drape 38 covers wound insert 34 and wound 26, and forms a space 50 between drape 38 and wound 26 (e.g., wound surface 42).

Apparatus 14 can comprise, for example, a vacuum source configured to be actuatable (and/or actuated) to apply negative pressure (e.g., via conduit 22) to wound dressing 18, a fluid source configured to be actuatable (and/or actuated) to deliver (e.g., via conduit 22) a fluid (for example, an instillation fluid such as a medicinal fluid, antibacterial fluid, or an irrigation fluid) to wound dressing 18. Wound treatment apparatus 14 may further comprise multi-conduit connector apparatus 1000 depicted in FIG. 2 and FIG. 3. System 10 can be implemented and/or actuated and/or coupled to patient 30 in any of various configurations and/or methods similar to those described in the prior art. For example, various wound therapy systems and components are commercially available through and/or from KCI USA, Inc. of San Antonio, Tex., U.S.A., and/or its subsidiary and related companies (collectively, "KCI").

Conduits 22, 450, 460 can comprise a single lumen conduit (e.g., switched between a vacuum source and/or a fluid source and apparatus 14), or can comprise multiple single-lumen conduits or a multi-lumen conduit such that, for example, fluid can be delivered and/or negative pressure can be applied to wound dressing 18 individually and/or simultaneously. Additionally, conduits 22, 450, 460 can comprise, for example, multiple lumens (e.g., as in a single conduit with a central limit for application of negative pressure and/or fluid delivery and one or more peripheral lumens disposed adjacent or around the central lumen such that the peripheral lumens can be coupled to a pressure sensor to sense and/or detect a pressure or negative pressure between drape 38 and surface 42 (e.g. in space 50), as described in the Hunt and Boynton patents incorporated above.

In the embodiment shown, system 10 further comprises a wound dressing connection pad 54 configured to be coupled (and shown coupled) to conduit 22. One example of a suitable connection pad 54 is the "V.A.C. T.R.A.C.® Pad," commercially available from KCI. One example of a suitable drape 38 includes the "V.A.C.® Drape" commercially available from KCI.

Figure 2:
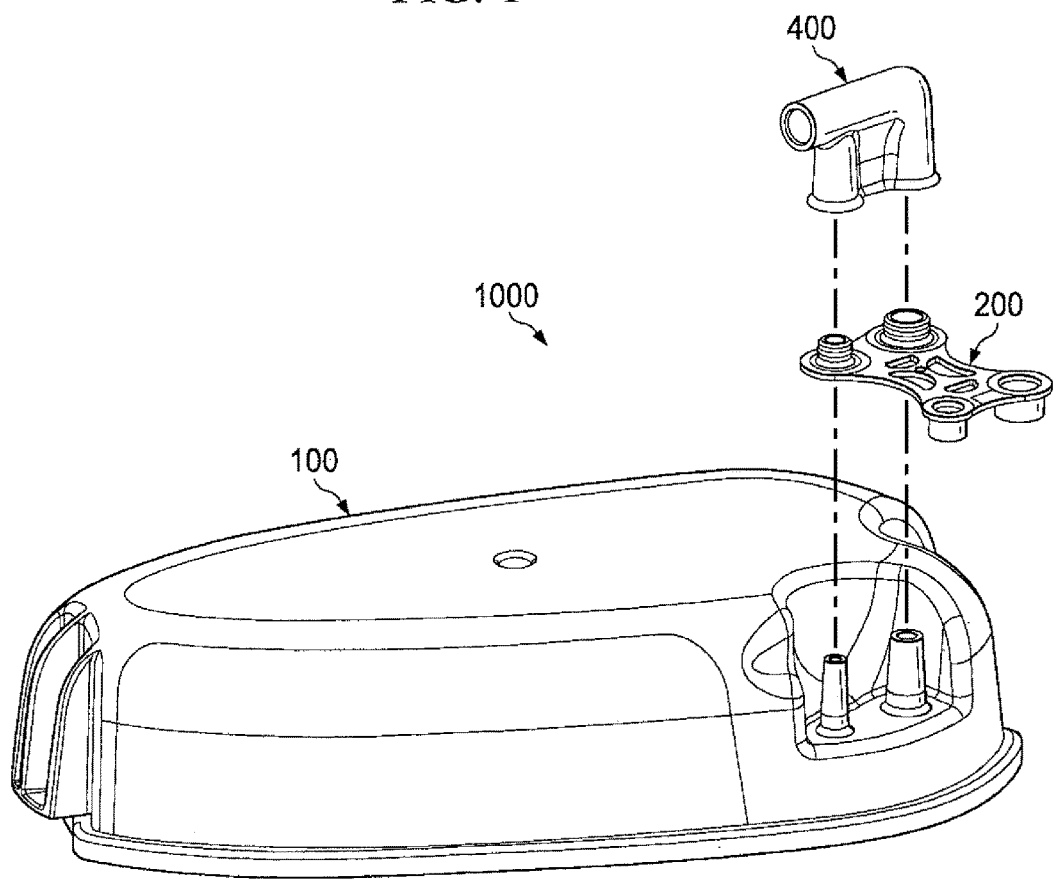
FIG. 2 depicts an exploded view of one embodiment of the present multi-conduit connector, canister lid, cap sleeve, and multi-conduit housing.
Figure 3:
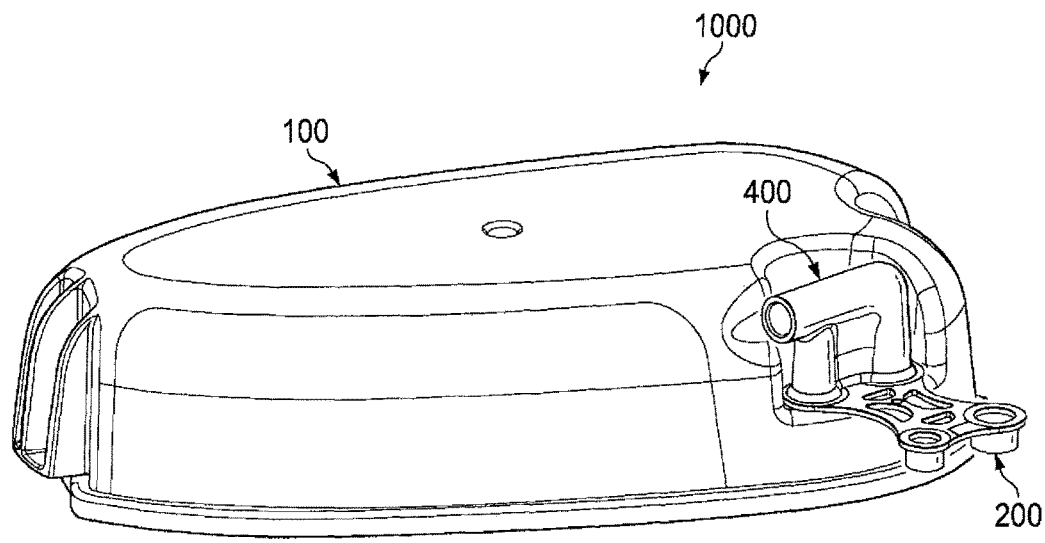
FIG. 3 depicts an assembly view of the multi-conduit connector, canister lid, cap sleeve, and multi-conduit housing.

Turning now to FIG. 2 and FIG. 3, one example of a multi-conduit connector apparatus 1000 is shown that comprises embodiments of a canister lid 100, a cap sleeve 200, and a multi-conduit housing 400 is shown. FIG. 2 shows an exploded view, while FIG. 3 shows an assembly view in which canister lid 100, cap sleeve 200, and multi-conduit housing 400 are coupled together. In the embodiment shown, cap sleeve 200 is placed over nipples 110, 120 on canister lid 100. Multi conduit housing 400 is placed over canister lid 100 and cap sleeve 200.

In some embodiments, canister lid 100, cap sleeve 200, and/or multi-conduit housing 400 may be comprised of rubber or plastic. In some embodiments, canister lid 100, cap sleeve 200, and multi-conduit housing 400 may be designed for a single use.

Figure 4:
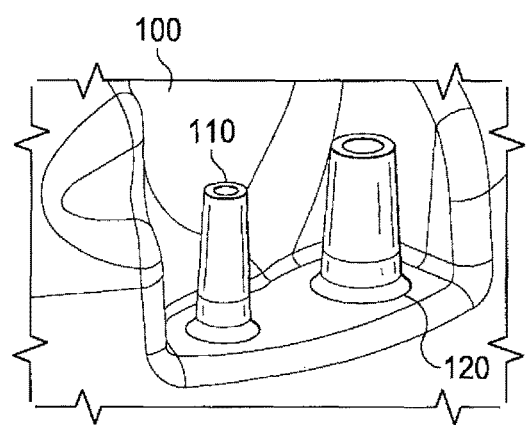
FIG. 4 depicts a perspective view of a portion of the canister lid of FIGS. 2 and 3.

Referring now to FIG. 4, an example of a canister lid 100 is shown. Other features of a canister lid not relating to the embodiments of the invention disclosed are not pictured for the sake of clarity. Canister lid 100 comprises first nipple 110 and second nipple 120. First nipple 110 may be configured to be coupled to a first outlet 451 shown in FIG. 7. Second nipple 120 may be configured to be coupled to a second outlet 461 shown in FIG. 7.

In some embodiments, first nipple 110 is configured to be coupled to a vacuum pump, a pressure sensor, or both. In some embodiments, second nipple 120 is configured to be coupled to an exudate receptacle. In other embodiments second nipple 120 is configured to be coupled to a source of medicaments.

Figure 5:
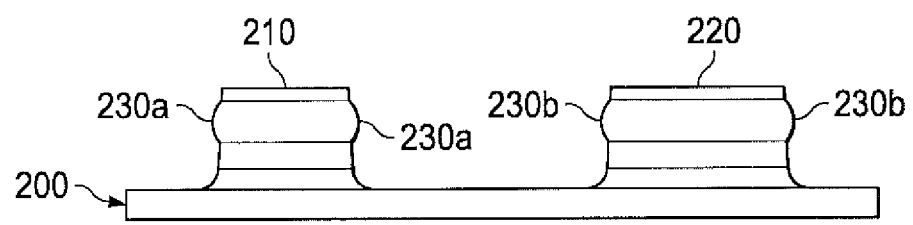
FIG. 5 depicts a side view of one embodiment of the present cap sleeve.

Referring now to FIG. 5, an example of a cap sleeve 200 is shown. Cap sleeve 200 comprises a first annular sleeve 210 and a second annular sleeve 220. First annular sleeve 210 and second annular sleeve 220 comprises a first clearance shoulder 230a on the outer surface of the sleeve. Second annular sleeve 220 comprises a second clearance shoulder 230b on the outer surface of the sleeve. Some embodiments of cap sleeve 200 may comprise a hinge and a lid (not shown) for each annular sleeve 210, 220 coupled to the hinge. Other embodiments may have a separate lid piece (not shown) for the annular sleeves 210, 220.

Figure 6:
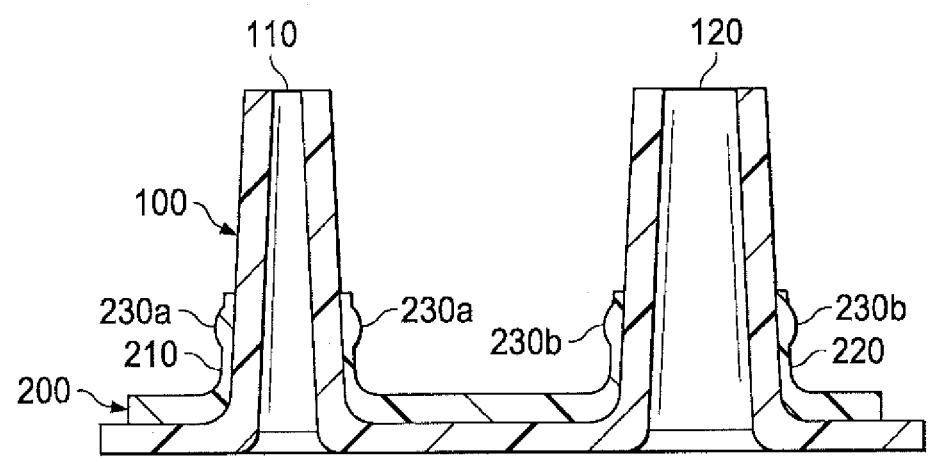
FIG. 6 depicts a side cross-sectional view of the cap sleeve of FIG. 5 coupled to the portion of the canister lid of FIG. 4.

Referring now to FIG. 6, a sectional assembly view of canister lid 100 of FIG. 4 and cap sleeve 200 of FIG. 5 is shown. Cap sleeve 200 is coupled to canister lid 100. In some embodiments, cap sleeve 200 may be removably coupled to canister lid 100. In other embodiments, cap sleeve 200 may be permanently affixed to canister lid 100. First annular sleeve 210 engages first nipple 110. Second annular sleeve 220 engages second nipple 120. Annular sleeves 210, 220 may be substantially in the shape of a circular ring in some embodiments. In other embodiments, annular sleeves 210, 220 may be substantially in the shape of a triangular ring, a square ring, or any other ring shape.

Referring now to FIG. 7, a sectional view of multi-conduit housing 400 is shown. Multi-conduit housing 400 comprises a first port 410 and a second port 420. First port 410 is configured to engage first nipple 110. Second port 420 is configured to engage second nipple 120. First port 410 comprises engagement tab 430 and a plurality of sealing ridges 440. Second port 420 comprises engagement tab 430 and a plurality of sealing ridges 440. Engagement tabs 430 are configured to engage clearance shoulders 230a, 230b. Sealing ridges 440 are configured to engage first nipple 110 and second nipple 120. In some embodiments, engagement tab 430 and sealing ridges 440 are made of a deformable material, including but not limited to rubber or plastic.

Ports 410, 420 are structural elements of multi-conduit housing 400 that are configured to be coupled to nipples 110, 120. Ports 410, 420 are substantially the inverse shape of the corresponding nipples 110, 120. For example, in some embodiments nipples 110, 120 are substantially in the shape of a frustum. In these embodiments, corresponding ports 410, 420 are also in the shape of a frustum. Nipples 110, 120 and ports 410, 420 may also be in the shape of cylinders, cones, prisms, or any other shape about which a seal can be created.

Multi-conduit housing 400 further comprises a first conduit 450 and a second conduit 460. First conduit 450 is configured to be coupled to a wound site. Multi-conduit housing 400 further comprises a first outlet 451. In some embodiments, first outlet 451 is configured to be coupled to first nipple 110. First conduit 450 is in fluid communication with first outlet 451.

Second conduit 460 is configured to be coupled to a wound site and further comprises a second outlet 461. In some embodiments, second outlet 461 is configured to be coupled to second nipple 120. First conduit 450 and second conduit 460 may be coaxial or parallel. Second conduit 460 is in fluid communication with second outlet 461.

Referring now to FIG. 8, a sectional assembly view of canister lid 100, cap sleeve 200, and multi-conduit housing 400 of FIG. 3 is shown. Cap sleeve 200 is coupled to canister lid 100. In some embodiments, cap sleeve 200 may be removably coupled to canister lid 100. In other embodiments, cap sleeve 200 may be permanently affixed to canister lid 100. First annular sleeve 210 engages first nipple 110. Second annular sleeve 220 engages second nipple 120.

Multi-conduit housing 400 engages both cap sleeve 200 and canister lid 100. First port 410 engages first nipple 110. First outlet 451 is in fluid communication with first nipple 110. Second port 420 engages second nipple 120. Second outlet 461 is in fluid communication with second nipple 120.

Engagement tab 430 engages clearance shoulders 230a, 230b, creating a seal between first port 410 and first annular sleeve 210, and also creating a seal between second port 420 and second annular sleeve 220. Sealing ridges 440 engage first nipple 110, creating a seal between first port 410 and first nipple 110. Sealing ridges 440 also engage second nipple 120, creating a seal between second port 420 and second nipple 120.

Other embodiments of this disclosure comprise only canister lid 100 and multi-conduit housing 400. First nipple 110 further comprises first clearance shoulder 230a. Second nipple 120 also further comprises second clearance shoulder 230b.

The arrangement in FIG. 8 provides a user with tactile and audible feedback that a connection has been made. In some embodiments, cap sleeve 200 is coupled to canister lid 100 during the manufacturing process. In other embodiments, cap sleeve 200 is installed by a user. In a hospital or clinical setting, a user may engage multi-conduit housing 400 with first nipple 110 and second nipple 120. The user may apply a downward force to multi-conduit housing 400 until engagement tabs 430 passes clearance shoulders 230a, 230b and can move no further. In some embodiments, an audible sound may be heard once multi-conduit housing 400 is fully engaged.

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of this invention.

We claim:

1. A canister connector apparatus comprising:
    a lid having a first nipple and a second nipple;
    a cap sleeve having a first annular sleeve configured to engage the first nipple and a second annular sleeve configured to engage the second nipple; and
    a conduit housing configured to engage the lid and having a first port with a plurality of sealing ridges configured to create a seal with the first nipple when engaged with the first nipple and a second port with a plurality of sealing ridges configured to create a seal with the second nipple when engaged with the second nipple.

2. The apparatus of claim 1, wherein a conduit is fluidly coupled to the first port and in fluid communication with the first nipple.

3. The apparatus of claim 2, wherein the conduit is fluidly coupled to a wound dressing.

4. The apparatus of claim 2, wherein the conduit comprises a single lumen.

5. The apparatus of claim 2, wherein the conduit comprises multiple lumens.

6. The apparatus of claim 1, wherein a conduit is fluidly coupled to the second port and in fluid communication with the second nipple.

7. The apparatus of claim 6, wherein the conduit is fluidly coupled to a wound dressing.

8. The apparatus of claim 6, wherein the conduit comprises a single lumen.

9. The apparatus of claim 6, wherein the conduit comprises multiple lumens.

10. The apparatus of claim 1, wherein:
    a first conduit is fluidly coupled to the first port and in fluid communication with the first nipple; and
    a second conduit is fluidly coupled to the second port and in fluid communication with the second nipple.

11. A system for treating a wound comprising:
    a wound dressing;
    a first conduit and a second conduit each having a first end configured to be fluidly coupled to the wound dressing and a second end; and
    an apparatus for treating the wound including a canister apparatus comprising:
        a lid having a first nipple and a second nipple;
        a cap sleeve having a first annular sleeve configured to engage the first nipple and a second annular sleeve configured to engage the second nipple; and
        a conduit housing configured to engage the cap sleeve and having a first port configured to be fluidly coupled to the second end of the first conduit and having a plurality of sealing ridges configured to create a seal with the first nipple when engaged with the first nipple, and a second port configured to be fluidly coupled to the second end of the second conduit and having a plurality of sealing ridges configured to create a seal with the second nipple when engaged with the second nipple.

12. The system of claim 11, wherein the apparatus further comprises a vacuum source configured to be fluidly coupled to the first nipple.

13. The system of claim 11, wherein the apparatus further comprises a fluid source configured to be fluidly coupled to the second nipple.

14. The system of claim 11, wherein the first annular sleeve includes a first clearance shoulder and the second annular sleeve includes a second clearance shoulder, each configured to engage the cap sleeve when the conduit housing engages the cap sleeve.

15. The system of claim 11, wherein the first port includes a first engagement tab and the second port includes a second engagement tap, each configured to engage the conduit housing when the conduit housing engages the cap sleeve.

16. The system of claim 11, wherein:
the first annular sleeve includes a first clearance shoulder configured to engage a first engagement tab of the first port when the conduit housing engages the cap sleeve; and
the second annular sleeve includes a second clearance shoulder configured to engage a second engagement tab of the second port when the conduit housing engages the cap sleeve.

17. A method for treating a wound comprising:
coupling a wound dressing to a wound;
fluidly coupling a first end of a first conduit and a first end of a second conduit to the wound dressing;
providing an apparatus including a canister apparatus having:
  a lid having a first nipple and a second nipple;
  a cap sleeve having a first annular sleeve and a second annular sleeve; and
  a conduit housing having a first port and a second port, each having a plurality of sealing ridges;
engaging the first annular sleeve with the first nipple and the second annular sleeve with the second nipple;
fluidly coupling the first port with the first nipple and the second port with the second nipple;
fluidly coupling a second end of the first conduit with the first port and a second end of the second conduit with the second port; and
treating the wound with the apparatus.

18. The method of claim 17, wherein fluidly coupling the first port with the first nipple and the second port with the second nipple comprises:
inserting the first nipple into the first port so that the plurality of sealing ridges engage the first nipple and the second nipple into the second port so that the plurality of sealing ridges engage the second nipple; and
engaging a first clearance shoulder of the first sleeve with a first engagement tab of the first port and a second clearance shoulder of the second sleeve with a second engagement tab of the second port to secure the conduit housing to the lid.

19. The method of claim 17, wherein the apparatus further comprises a vacuum source, and treating the wound with the apparatus further comprises fluidly coupling the vacuum source to the first nipple to supply reduced pressure to the wound.

20. The method of claim 17, wherein the apparatus further comprises a source of fluid, and treating the wound with the apparatus further comprises fluidly coupling the source of fluid to the second nipple to supply fluid to the wound.

21. The method of claim 20, wherein the fluid comprises at least one of medicinal fluid, antibacterial fluid, or irrigation fluid.

22. The method of claim 17, wherein the apparatus further comprises a vacuum source, and a fluid source and treating the wound with the apparatus further comprises fluidly coupling the vacuum source to the first nipple to supply reduced pressure to the wound and fluidly coupling the source of fluid to the second nipple to supply fluid to the wound.

* * * * *

UNITED STATES PATENT AND TRADEMARK OFFICE
CERTIFICATE OF CORRECTION

PATENT NO. : 9,956,328 B2
APPLICATION NO. : 14/930479
DATED : May 1, 2018
INVENTOR(S) : Justin Alexander Long et al.

Page 1 of 1

It is certified that error appears in the above-identified patent and that said Letters Patent is hereby corrected as shown below:

In the Claims

At Column 9, Claim number 15, Line number 11, replace "tap" with "tab"

Signed and Sealed this
Fourth Day of December, 2018

Andrei Iancu
*Director of the United States Patent and Trademark Office*